United States Patent [19]

Kamentsky

[11] Patent Number: 4,647,531

[45] Date of Patent: Mar. 3, 1987

[54] GENERALIZED CYTOMETRY INSTRUMENT AND METHODS OF USE

[75] Inventor: Louis A. Kamentsky, Weston, Mass.

[73] Assignee: Ortho Diagnostic Systems, Inc., Raritan, N.J.

[21] Appl. No.: 577,448

[22] Filed: Feb. 6, 1984

[51] Int. Cl.[4] .............................................. G01N 1/28
[52] U.S. Cl. ....................................... 435/7; 435/289; 435/291
[58] Field of Search ................... 435/7, 30, 34, 289, 435/291, 292, 293, 299, 300, 301, 808

[56] References Cited

U.S. PATENT DOCUMENTS

| | | | |
|---|---|---|---|
| 4,142,859 | 3/1979 | Shaffer | 435/291 X |
| 4,174,384 | 11/1979 | Ullman et al. | 435/7 X |
| 4,224,405 | 9/1980 | Hijikata | 435/291 X |
| 4,318,981 | 3/1982 | Burd et al. | 435/7 |
| 4,368,047 | 1/1983 | Andrade et al. | 435/7 X |
| 4,385,113 | 5/1983 | Chappelle et al. | 435/291 X |
| 4,399,099 | 8/1983 | Buckles | 435/7 X |
| 4,444,879 | 4/1984 | Foster et al. | 435/7 |
| 4,474,878 | 10/1984 | Halbert et al. | 435/7 |
| 4,477,576 | 10/1984 | Deutsch et al. | 435/7 X |
| 4,478,817 | 10/1984 | Campbell et al. | 435/7 X |

Primary Examiner—Alan Cohan
Assistant Examiner—John A. Rivell
Attorney, Agent, or Firm—Mark A. Hofer

[57] ABSTRACT

A generalized cytometry instrument for measuring the kinetic properties of live cells. Cells are immobilized on a surface and their positions determined and stored in memory by a central control computer. The cells are subsequently illuminated and an optical interaction detected. By taking many measurements of many cells, each of whose position and respective data is stored permitting subsequent reexamination and determination of activity as a function of time, respectively; the kinetic properties of large populations of cells may be studied in the presence of a variety of stimulating environments. Such stimulations may arise from contact with various reagents, including antigens, mitogens and peptides as well as electrical and mechanical perturbations.

31 Claims, 2 Drawing Figures

GENERALIZED CYTOMETRY INSTRUMENT AND METHODS OF USE

FIELD OF THE INVENTION

This invention relates generally to instruments for measuring cells and specifically relates to computer controlled instruments employing laser light sources for the dynamic or kinetic monitoring of functional properties of live biological cells over time.

BACKGROUND OF THE INVENTION

The detection and characterization of certain types of biological cells has proven useful in identifying and discriminating between certain disease states. To date, such interrogations have been performed by three classes of instruments, those employing standard microscopy techniques, those utilizing pattern analysis techniques, and those based on flow cytometry technology.

Standard microscopy is the oldest of these techniques and conceptually the simplest to understand. Standard microscopy optically examines, by means of a series of glass lenses in the objective and ocular portions of a microscope, cells placed on the surface of a transparent support surface or slide. A field encompassing the cells of interest is exposed to visible or ultraviolet light and the cells' optical absorption or fluorescence is observed or manually measured using a photodetector. Signal changes can then be related to altered levels of cellular constituents such as proteins or nucleic acids. These procedures tend to be tedious, time consuming and are difficult to apply to living cells. Hence, although useful for obtaining morphological information, they are inappropriate for deriving dynamic or time varying information from biological cells. It is an object of the present invention to overcome these inherent, standard microscopy limitations.

Subsequently, pattern analysis techniques were developed to provide the capability to scan, en masse, a plurality of conventionally stained cells which have been flattened out on slides and to process the resulting data. As a result, these techniques have permitted the development of a class of clinical laboratory instruments which have automated certain manual procedures previously employed in standard microscopy. Pattern analysis has, however, because of the staining techniques been confined to measuring morphological properties of nonviable cells rather than biophysical properties of live cells and their constituents. Hence, its usefulness has been limited to differentiating cell types in heterogeneous populations.

It is an object of the present invention to provide a new class of apparatus and methods utilizing same for measuring individual, kinetic or time varying biophysical properties of live cells and cellular constituents; properties which cannot be determined with present pattern analysis techniques.

Still another well-known class of clinical and research laboratory, light based instruments include those based on the so-called flow cytometry technology. Typically, these instruments hydrodynamically focus fluid suspended cells into a single file stream for passage through an examination zone. While in the zone, the cells interact with impinging light from a focused light source, ideally a laser. One or more optical interactions of the cells and the light are measured and may include, for instance, multiple wavelength absorption, scatter as a function of angle, fluorescence as a function of wavelength, polarization, and the like. This class of instruments permits the study of living cells in addition to those which have been chemically treated. Flow cytometry techniques also enable certain constituents or structures, particularly those present on the cell surface, to be quantitatively characterized at cell rates of a thousand or more cells per second. With such great sampling rates, the size, shape and number of large populations of cells may be readily studied thereby permitting the biologist to gain statistically significant information about the numerically small subpopulations of cells comprising the heterogeneous population.

Flow cytometry techniques, in addition to the previously described techniques, however, commonly suffer from an inability to practically measure the kinetic properties of live cells in large heterogeneous populations. They are also unsuitable for the practical study of the flow of biological information in and between living cells such as neurons, blood cells and the like. This inability stems predominantly from the instruments' incapacity to maintain the identity of each cell measured and/or the instruments' inability to perform the measurements over a cellularly significant passage of time in the short of time interval during which the cell is present in the examination zone.

It is an object of the present invention to provide means and methods for studying the kinetic properties of live cells in large heterogeneous populations.

It is a related object of the present invention to provide means whereby the exchange of biological information inter and intra-cellularly may be measured.

It is a further object of the present invention to provide means and methods which do not employ instruments of the classes previously discussed.

It is a related object of the present invention to provide an instrument which relies upon the sensitivity provided by cells in order to detect the presence or absence of materials in a fluid brought into contact with the cells and thereby also provide improved sensitivity in the detection of such materials.

It is a yet further object of the present invention to provide an apparatus capable of detecting specific types of cells which may be differentiated by their reactivity with and sensitivity to reagents brought into contact with those cells.

It is a still further object to provide apparatus and methods capable of performing cellular indentification and measurements in the requisite time frames to obtain the kinetic information desired.

SUMMARY OF THE INVENTION

In accordance with the principles and objects of the present invention, there is provided a generalized cytometry instrument for the repetitive measuring of various properties of live cells. The instrument comprises a surface means for immobilizing the cells to be studied. In a preferred embodiment, the cells will be immobilized in a gel capable of supporting cell growth. The instrument further comprises cell locating means for determining the position of at least two cells of the cellular population immobilized on said surface means. Ideally, the cell locating means comprises a helium neon laser plus associated cell presence identification and location data handling capability. In addition, the instrument provides for illuminating means whereby an immobilized cell may be illuminated and the response to said illumination observed and recorded by detecting means. Such responses may include fluorescence, phase contrast, interference effects, light scatter, absorption, polarization and the like.

The instrument further comprises means for controlling which is coupled to the cell locating means and to memory means for recording the position of an immobilized cell. The means for controlling is further coupled to the illuminating means and the detecting means so that once a cell is located, the illuminating means is activated and the cellular response, observed by said detecting means, is recorded in the memory means and identified with the respective cell from which the data was derived.

A preferred embodiment of the generalized cytometry instrument will further comprise translocating means whereby multiple immobilized cells may be studied. Such translocating means will ideally operate by moving the surface means in cooperation with said means for controlling and said cell locating means, however; movement of the illuminating means, the means for detecting, and said cell locating means across a stationary immobilization means surface is also contemplated.

The generalized cytometry instrument may be employed with great versatility to test various types of cells with standard reagents, or to test standard cells with various types of reagents. For instance, patient cells may be immobilized on the surface means and reacted with a first material or antigen and the resultant first activation response measured. This method is particularly useful when the patient cells are T-lymphocytes whose sensitivity to a particular antigen is to be studied. The cells are then subsequently reacted with a general mitogen and a second activation response detected. By relating the first and second activation responses, one may determine the general state of sensitization of the cells, and the specific state of sensitization with respect to the first material or particular antigen. Depending on the type of detection to be employed, i.e. fluorescence etc., the cells may require appropriate treatment such as treatment with a transmembrane or fluorescent dye in the case of fluorescence detection. They may then be subsequently reacted with a second reagent to cause an activation event or functional change in the cells causing detectable changes in the fluorescent dye, or other detectable label. Various orders of the reaction steps are contemplated as is the testing of reagent cells with patient fluid samples for the detection of specific materials contained therein.

BRIEF DESCRIPTION OF THE DRAWINGS

Further understanding of the present invention may be had by reference to the drawings wherein.

DETAILED DESCRIPTION AND BEST MODE

Figure 1:
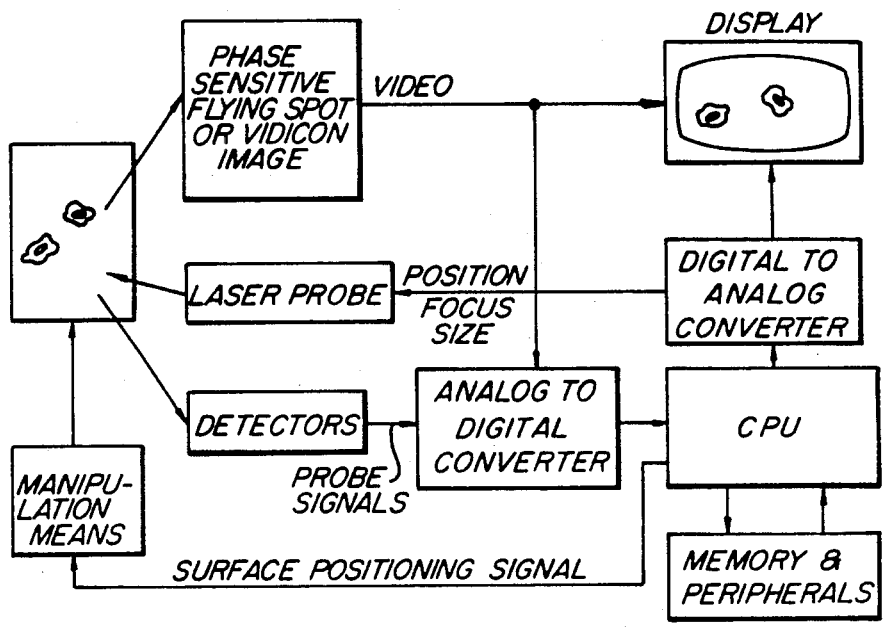
FIG. 1 illustrates in block diagram the operation of the preferred embodiment of the present invention.

In order to accomplish the objectives of the present invention, multiple interrogation of live cells is required. To do this, the cells must be immobilized upon some type of surface in such a manner that their viability is maintained and their position definable so that multiple interrogations or probing of cellular response may be performed. This may be expeditiously accomplished in a variety of ways. For instance, a preferred embodiment will immobilize the cells to be studied on an optical stage by means of suspending the cells in a gel. The gel will be ideally selected to maintain cellular viability by supplying vital nutrients in an appropriate environment and to permit the application of test reagents or other types of stimulation to the cells. Such a gel may be, for instance, an agarose sheet employed in a manner well-known by those skilled in the art.

Alternatively, the cells may be attached by immunological reaction with antibodies which themselves have been immobilized on the immobilization surface. These antibodies, preferably of monoclonal origin in order to maximize their specificity, may be appropriately selected to effect a prescreening of a heterogeneous population of cells by reacting only with a specified subclass of cells having a predetermined antigenic determinant on the cellular surface. Such a preselection may advantageously increase the efficiency of the entire general cytometry instrument by eliminating those cells present in a heterogeneous population which are of substantially no interest. Alternatively, the antibody may be selected to nonspecifically react with all cells of the sample. The surface means having the antibody immobilized cells thereon will be advantageously constructed to also contain a solution for maintaining cellular viability in contact with the cells. Typically, such a solution may be a cell culture media selected so as to avoid having characteristics which would otherwise interfere with the operation of the generalized cytometry instrument.

As intimated, the capability to perform multiple interrogations is a requisite to the operation of the generalized cytometry instrument of the present invention. Accordingly, a necessary element is the cell locating means for determining the position of at least two cells immobilized on said surface means. The cell locating means must be capable of providing x-y coordinates for the cells with sufficient accuracy so that the cells may be subsequently located therewith. In those cases Where the cells may be present at different heights, for instance, if the immobilizing means comprises a gel, then resolution on the z axis may also be advantageous, particularly if a non-collimated, small diameter illumination light source is employed. Conversely, employing a collimated, large diameter (i.e. greater than cell diameter) light beam will obviate the need for resolution on the z-axis. The cell locating means will ideally comprise a helium neon laser and associated cell presence identification and location data handling circuitry. Such a laser is preferred for its ready availability, dependable characteristics and low cost. As may be readily appreciated, the cell locating means may advantageously utilize technology associated with flying spot type scanners which are effective cell locators. Similarly, vidicon image technology may be suitably employed. The cell location data is electronically communicated to the CPU or central processing unit of the generalized cytometry instrument. As will be readily appreciated by those skilled in the art, such communication may necessitate the conversion of analog to digital type signals, such as by an A-D converter, for appropriate handling by the CPU.

The central processing unit controls the overall operation of the generalized cytometry instrument. Ideally, the CPU may functionally be a small computer or microprocessor which will preferably be subject to operator control via appropriate programming in accordance with the testing modes desired. The CPU will advantageously communicate with accessory memory means, unless such memory means is or becomes part of the CPU itself as integrated circuit technology advances, as well as peripherals such as printers, CRT displays and the like, through suitable circuitry.

Once a cell's location has been identified by the cell locating means and its location stored in the memory by the CPU, the CPU will ideally activate the illuminating means for providing focused illumination to the immobilized cell. The combination of cell location and illumination may be accomplished separately (i.e. locate all cells and then illuminate all cells) or together (i.e. locate a cell, illuminate the cell, locate the next cell etc.). Cellular illumination may be advantageously accomplished by energizing a laser probe, for instance, an argon-ion laser of suitable power. The preferred embodiment will control the laser probe so that it provides illumination to the position associated with the cell by illuminating the cell with a "spot of light" of a diameter commensurate with that of the cell. Focusing of the laser probe may be important if the cells have different z-axis coordinants associated therewith and indeed, may be critical depending on the type of cellular-optical response to be detected, such as phase or scatter variations. In its simplest embodiment, however, the illumination means will merely provide collimated light with a diameter greater than that of cell, i.e. 20 micron or thereabouts. Indeed, the cell locating means and the illumination means may be the same light source, such as an argon-ion laser, which is operated at different power levels suitable for locating and illuminating purposes respectively.

Operating in conjunction with the illuminating means, will be means for detecting the cell's optical response and may comprise devices such as photodetectors and the like, which are arranged in number, kind and manner for observing the cell's interaction to said illuminating means. For instance, if cellular fluorescence is to be detected (occasioned for instance by treatment with a fluorescently labeled antibody specific for a cell associated antigen or a fluorescent dye which will become associated with the cell), then the detector will be advantageously selected to respond to the fluorescent wavelength of interest and be insensitive to other wavelengths. This selective sensitivity may be readily obtained by the use of spectral filters in conjunction with photomultiplier tubes via well-known methods. Alternately, the amount of light scatter may be measured by arranging the photodetectors at the angular relationships for which scatter may be characteristic of specified cells of interest. The scatter characteristics, and arrangement of light scatter detectors, comprises a technology well-known in the field of flow cytometry instruments and full reference by incorporation is made to U.S. Pat. Nos. 4,202,625 to Weiner et al., 4,284,412 to Hansen et al., and 4,325,706 to Gershmen et al. Those references will also be suitable for teaching appropriate detector arrangements for measuring natural (UV) absorption as well as fluorescence. In any event, the method of response detection, i.e. fluorescence scatter etc., will be advantageously chosen in view of sensitivity taking into account S/N ratios as well as the type of reagents used to 'activate' the cells and the responsive effects to be detected and data desired. Further, the measurement time per cell will be ideally carefully tailored in view of the number of sites (cells to be examined) to advantageously improve or optimize the sensitivity. A further advantage of this system is that the measurement time per cell can be made inversely proportional to the number of fluorescent molecules on or within each cell by integrating the light until a given integral of light is reached.

As is well-known, many of the optical arrangements alluded to earlier may be constructed using standard or optional arrangements available with a variety of microscopes. For instance, an inverted microscope may be readily modified with shutter means operated by the controlling means for regulating the operation of the detector means in response to illumination of the immobilized cells.

The means for controlling or central processing unit will be coupled to the cell locating means, the illumination means and the means for detecting in order to facilitate and coordinate location of the cell, illuminating the cell with the appropriate quantity and quality of light required, and detecting the optical response of the cell in response to the illumination. The data will then be stored in memory means in a manner such that subsequent illuminations and optical observations of the same cell can be compared with prior observations. The CPU will advantageously incorporate additional data handling capabilities whereby the optical response observations may be summed or otherwise manipulated to provide an overall picture of cellular activity in the subcells of interest. For instance, the apparatus as described will be capable of identifying various types of cellular populations within a heterogeneous population and, after the application of various stimulations to the cells, it may be expected that some of these subpopulations will react differently. These differences will be recorded and should be subject to suitable expression such as by histogram or other graphical/numerical display means.

Figure 2:
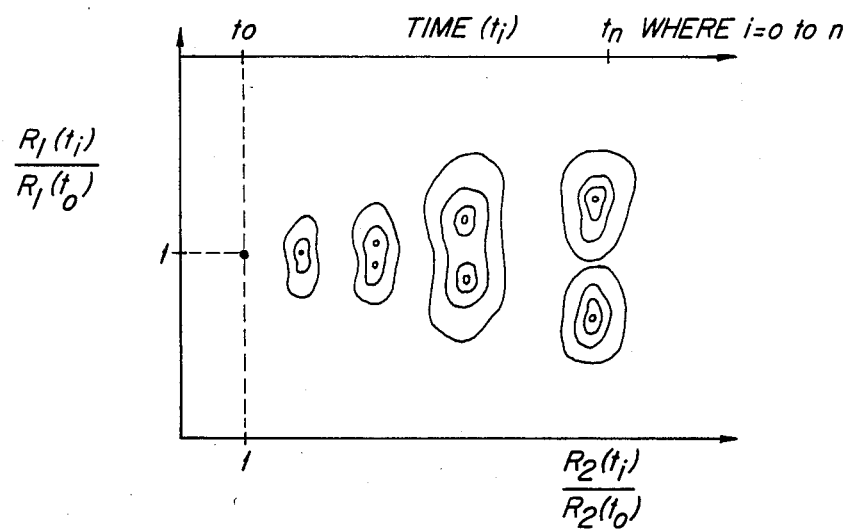
FIG. 2 graphically depicts how kinetic cellular information derived by the apparatus of the present invention may be displayed.

One potential method of displaying data is shown in FIG. 2. The display shows populations of cells displayed in accordance with two separately measured responses $R_1$ and $R_2$, specifically the change in ratio of each cellular response at time $t_i$ to the initial response at time $t_o$ as a function of time. At time $t_o$, $R_1(t_o)/R_1(t_o) = R_2(t_o) = 1$ and all cells may be represented by a dot. As time advances, cellular response becomes measurable and distinguishable on a per cell basis, i.e. at least one of the response ratios no longer equals one. This change may be represented by contours such as shown in FIG. 2 whereby functionally discrete populations become separately resolved over time or, by displaying each cell as a separate dot, or isometrically. Still other variations may readily suggest themselves to one skilled in the art. Any display providing cellular response as a function of time will be suitable.

It is to be understood that the term display includes both pictorial representations such as that shown in FIG. 2 as well as any other type of data rendering format including printed representations of cell numbers, responses and the like. The present invention further contemplates the use of electronic windows, known with flow cytometry instruments, for the purposes of isolating cellular subpopulations exhibiting certain display parameters and providing data with respect such 'enclosed' cellular subpopulations such as cell numbers, and the like.

The controlling means may also advantageously provide for the suitable employment of other peripherals as necessary to provide a permanent record of the response observations and to provide numerical data or statistical manipulations as appropriate.

In order to provide the generalized cytometry instrument with optimum utility, it will be advantageous to couple the cell locating means either directly or, preferably through the controlling means, with translocating means. The translocating means will provide the electromechanical forces necessary whereby multiple cells may be probed. These electromechanical forces, in the preferred embodiment will be expeditiously provided by coupling the surface means to a stepping motor or other electromechanical device capable of moving the surface. Alternatively, the translocating means may move the cell locating means, illuminating means and detecting means over a stationary surface means. For readily apparent reasons of simplicity, the movement of the surface means is preferred. It is also contemplated that the translocating means may assist in focusing operations when such are needed by providing suitable movement in all three coordinate directions.

In order to fully take advantage of the capabilities of the generalized cytometry instrument of the present invention, it may be found advantageous to provide additional manipulation means capable of adjusting the macro or micro environment of the immobilized cells. For instance, such manipulation means should be capable of uniformly distributing a reagent to contact the cells for measurement of their response thereto. Alternately, in order to test individual cellular response, the manipulation means will advantageously be capable of chemically adjusting the environment of the individual cell of interest such as by applying a small amount of suitable reagent thereto or, be similarly capable of applying other suitable electrical or mechanical stimulations.

In order to provide the generalized cytometry instrument with still greater versatility, it may be found preferable to provide the system with dual resolution capabilities. For instance, a low resolution system, allowing for observation of very large populations, could provide a spot size of approximately 20 microns, a spacing of 10 microns, and a field size of 50 by 50 millimeters. A sample time on the order of one millisecond could be advantageously implemented in order to advantageously increase the S/N (signal to noise) ratio. The number of elements per field may ideally be approximately 5,000 by 5,000 thereby providing a one line, full-field, tracking time of 5 seconds and a cell examination rate of 100 per second or 10 milliseconds to find and examine each cell.

In contrast, a high resolution system may provide a 0.1 micron spacing, a 0.2 spot size, a field size of 40 microns by 40 microns and a sampling time of 10 microseconds. This would result in approximately 400 by 400 elements per field and a one field scanning time of 1.6 seconds. The high resolution system may also be advantageously capable of automatically maintaining a focus on a plane or on a cellular surface while the low resolution system will preferentially be capable of providing uniform illumination throughout the 10 micron spot.

As may be readily apparent, useful illumination wavelengths will be in the range of approximately 260 nM to 520 nM. Accordingly, detection of the cellular illumination response will preferably be one or more of the following methods performed simultaneously: absorption of the incident wavelength; forward scatter; and fluorescence and forward scatter with polarization, discrimination and wavelength discrimination at 260 nM–700 nM. The generalized cytometry instrument of the present invention may be further provided with an optical preview and set-up system, advantageously performed by an independent microscope system thereby allowing the operator the opportunity to inspect the surface means, and the cells immobilized thereon, prior to actually performing measurements.

As may be readily understood, the generalized cytometry instrument of the present invention provides great versatility for studying cellular interactions, as well as cellular reaction with various agents or reagents. For example, the cells may be contacted with a specific antigen or other material and their activation responses detected by detecting the cell's optical interactive response to illumination. The cells may then be subsequently reacted with a general mitogen or similar non-specific material and again their activation responses detected. Correlation between the activation responses will permit identification of various characteristics of cell types in the population. In quick summary, the generalized cytometry instrument would operate to find the position of the cell, illuminate the cell, detect the optical response or interaction and record same, reposition the surface means to find a position of a new cell and the process repeated. Alternately all cellular positions could be determined first and then their response at time to be determined as each cell is relocated. Either before or after the cells are located, the various test reagents may be added, the above processes repeated, and when the data collection is completed, it may be analyzed and displayed as appropriate.

Indeed, the versatility of such an instrument will be enormous, particularly when used in conjunction with fluorescence technology. For instance, cellular transmembrane potential may be studied using electric field sensitive dyes. If the electric field sensitive dyes chosen are fluorescent, then intracellular fluorescence may be monitored and related to the transmembrane potential property. Additional manipulation of cellular surface structures, such as by attachment of antigens, antibodies or other chemicals may detectably alter transmembrane potentials. Similarly transport modulatable dyes may provide information concerning membrane integrity, cellular viability or transmembrane potential. In like manner, fluorescence depolarization and anisotropy will provide valuable data regarding motions of cellular structure. Scatter measurements may be used to reveal structure morphology while variations in polarization could detect structure orientation. Further, the actual detection of specific cell surface structures or determinants-receptors, or intracellularly associated determinants-receptors may be accomplished using fluorescently tagged antibodies specific for the determinant, receptor or structure. Indeed, the sensitivity of measurement of small amounts of constituents such as the antibodies over that provided by the flow cytometry methods may be further improved by carefully tailoring the illuminating power and detection time per cell, especially while measuring each cell, to maximize the signal.to noise ratio and thereby obtain the required signal for improved measurement sensitivity.

Still other vital fascinating kinetic effects occuring among cells may be studied including the transmission of action potentials within and among cells, such as neurons, by utilizing the transmembrane potential sensitive dyes. Similarly, cellular transport mechanisms may be elucidated using transport modulatable dyes. By employing dye-to-dye, energy transfer type labeling mechanisms, the distance between molecules or structures, or even the movement of molecules or structures, may be measured since with this class of labels, the level of fluorescence is particularly sensitive to the intermolecular distance between the acceptor and donor dye moieties. See for instance, Stryer, L., Fluorescence Energy Transfer as a Spectroscopic Ruler, Am Rev. Biochem. 47:819–846 (1978). These energy transfer dyes will lend themselves well to the study of protein interactions of the cellular surface. Cell-to-cell communication by chemical transmitter substances may be readily studied by forcing the cells to collide by either mechanical or electrical means and then monitoring the movement of the substances, previously labeled by a specific dye. Other cellular substances such as DNA, RNA, enzymes and other proteins may also be labeled using constituent specific dyes which may be monitored by fluorescence or U.V. absorbance.

Still other valuable information may be obtained using the generalized cytometry instrument such as that pertaining to the correlation of the biophysical properties (via kinetic data) with cellular morphology (via the high resolution image of the cell being probed). Such abilities will further permit tracking the movement of cell surface proteins by either photobleaching or by following fluorescent probe movements. By utilizing transmembrane potential dyes or fluorescence depolarization in conjunction with scattering measurements, cell growth, differentiation and division may be correlated with morphology.

Other methods for use include the study of cell, sperm or bacteria movements as a function of externally supplied reagents, fields or presence of other cells. The kinetic capabilities of the instrument permit the monitoring of ionic, metabolic concentrations, transmembrane potentials, and the states of proteins as a function of the time and surrounding environment. Clearly, microelectrode probe stimulation or microinjection of reagents into or near cells can provide still additional valuable data. In some applications cells to be measured may be selected on the basis of their reactivity to one reagent and then are subsequently measured or their response detected after reaction with a second reagent.

The following are provided as application examples of the generalized cytometry instrument of the present invention to cell activation assays but are not to be construed as limitations of the generalized cytometry instrument's utility.

EXAMPLE 1

The generalized cytometry instrument can be applied to various diagnostic tests using patient blood cells or serum. For instance, patient blood cells are immobilized, treated with a fluorescent dye such as fluorescein diacetate (FDA) and then reacted with various antigens and mitogens. The generalized cytometry instrument is used to assay their response by following fluorescence anisotropy changes in each cell over time. See, for instance, Cercek, "Fluorescein Excitation and Emission Polarization Spectrum in Living Cells: Changes During the Cell Cycle", Biophysical J. 23:395–405 (1978). Alternately, the patient's serum containing soluble antigens or analytes, whose presence is to be determined, may be reacted with immobilized reagent cells capable of responding to the analytes or antigens whose presence or absence is to be determined. The cells may be expeditiously obtained by in vitro animal immunizations which yield reactive T-cells, capable of reacting to the presence of antigen or analyte to be tested. A typical reaction to the presence of antigen might be the change in transmembrane potential of the cell detectable by the increase in uptake of a suitable, charged fluorescent reagent. Further reference may be had to Shapiro et al., "Estimation of Membrane Potentials of Individual Lymphocytes by Flow Cytometry", PNAS Vol. 76, 11:5728–5730 (11/1979).

It should be noted that it is important to measure relative response of cells to two or more ligands, i.e. the analyte or antigen and a nonspecific mitogen. The ratio of fluorescence depolarization changes resulting from the application of each ligand can then be used as the basis for determining whether the patient has the antigen or antibody being tested for. For instance, detection of cancers having specified antigen or antigens associated therewith will be possible using a cancer associated antigen as the test reagent or patient sample and patient cells or reagent cells immunized for the cancer associated antigen, respectively.

The test is performed by measuring two or more kinetic responses or results for each active cell. Specifically, the cell is reacted with one ligand such as the particular antigen of interest, and then subsequently reacted with a fluorescently labeled probe and the cell's optical interaction to the illuminating means measured. Thereafter, the cells are reacted with the nonspecific ligand, i.e. mitogen, and then with the fluorescently labeled probe and their optical interaction again measured. The kinetic response of the cells to the specific antigen, and then the general mitogen may be appropriately ratioed to provide new indices regarding cellular function.

Alternately, the order of reaction may be reversed so that cellular response to the general mitogen is determined prior to cellular response to the specific antigen. If such an order is employed, it will most likely be found necessary to wash the cells of the general mitogen and dye prior to reactions with specific antigen. This necessary wash step makes the prior arrangement and order of reactions preferred. Still other possibilities are contemplated and include first reacting the cells with a fluorescently labeled probe and then monitoring the probe after treatments with the general and specific mitogens. This procedure may also advantageously eliminate separate steps for labeling and washing between treatments.

EXAMPLE 2

Cellular activation as a result of proteins coded for by oncogenes or virus may be studied by employing the generalized cytometry instrument of the present invention. It is known that specific blood cells can be activated and it is thought that this activation may, in some cases, be the result of proteins which are coded for by oncogenes or virus. Given the gene coding, which defines the activating proteins, synthetic peptides can be produced utilizing the peptide sequencing and synthesizing procedures and instruments now readily available and known. The synthetic peptides may be useful reagents for testing the immune status of patients with respect to cancer-like diseases or viral infections by monitoring cellular response. Indeed, an entire profile of synthetic peptide reagents could be employed to test patient cells. Such a modality could soon prove to be clinically quite useful for the diagnosis and monitoring of treatment, particularly with regard to cancer.

As may be readily appreciated, due to the enormous flexibility and versatility of the generalized cytometry instrument of the present invention, many variations will become readily apparent to those skilled in the art without departing from either the spirit or scope of the present invention.

What is claimed is:

1. A generalized cytometry instrument for the repetitive measuring of properties of live cells comprising:
   (a) surface means for immobilizing the cells to be studied;
   (b) cell locating means for determining the cellular location of at least two cells on said surface means;
   (c) illumination means for providing illumination to a located cell on said surface means;
   (d) means for detecting a response to said illuminating means;
   (e) means for controlling coupled to said cell locating means and to memory means where said cellular location may be stored, said means for controlling further coupled to said illumination means and said means for detecting whereby, in response to said cell locating means, said illumination means is activated and the response from said means for detecting is recorded in said memory means respectively with said cellular location; and
   (f) display means for presenting data stored in said memory means.

2. The generalized cytometry instrument as provided in claim 1 further comprising translocating means for providing comparative motion between the illumination means, means for detecting and said surface means, said translocating means acting in cooperation with said means for controlling and said cell locating means whereby different immobilized cells may be illuminated and their respective responses detected.

3. The generalized cytometry instrument as provided in claim 2 wherein the means for controlling further comprises signal conditioning means for altering signals to a form suitable for the respective locating, illuminating, detecting, memory and control means operations.

4. The generalized cytometry instrument as provided in claim 1 wherein the means for detecting detects an optical interaction selected from the group consisting of phase contrast, interference, light scatter, fluorescence, absorption, polarization, and any combination of the foregoing.

5. The generalized cytometry instrument as provided in claim 2 wherein the means for detecting detects an optical interaction selected from the group consisting of phase contrast, interference, light scatter, fluorescence, absorption, polarization, depolarization and any combination of the foregoing.

6. The generalized cytometry instrument as provided in claim 5 wherein the surface means further comprises an immobilizing agent selected from the group consisting of agarose and antibodies specific for a determinant associated with said cells to be immobilized.

7. The generalized cytometry instrument as provided in claim 6 wherein said cell locating means comprises a helium-neon laser, said illumination means comprises an argon-ion laser, and said means for controlling comprises a central processing unit.

8. The generalized cytometry instrument as provided in claim 1 wherein said display means presents cellular response data as a function of time.

9. A method for measuring the activation of a cell as an indication of sensitization to a substance comprising the steps of:
   (a) providing the cells whose sensitization is to be measured;
   (b) immobilizing said cells on surface means of a generalized cytometry instrument as described in claim 1;
   (c) reacting said cells with said substance;
   (d) locating a cell with said cell locating means;
   (e) illuminating said located cell with said illumination means and detecting a first activation response;
   (f) further contacting said cells with a general mitogen, locating said previously located cell, illuminating said cell with said illumination means and with said means for detecting measuring a second activation response; and
   (g) relating said first and said second activation responses to determine the state of sensitization of said cells to said particular substance.

10. The method of claim 9 wherein the generalized cytometry instrument further comprises translocating means for providing comparative motion between the illumination means, means for detecting and said surface means, said translocating means acting in cooperation with said means for controlling and said cell locating means whereby different immobilized cells may be illuminated and their respective responses detected.

11. The method as presented in claim 10 further comprising the step of contacting said cells at least once with a dye or a labeled probe whereby illumination from said illumination means interacts with said dye or labeled probe to provide a detectable activation response.

12. A method for measuring the activation of a cell as an indication of sensitization to a substance comprising the steps of:
   (a) providing the cells whose sensitization is to be measured;
   (b) immobilizing said cells on surface means of a generalized cytometry instrument as described in claim 1;
   (c) reacting said cells with a general mitogen;
   (d) locating a cell with said cell locating means;
   (e) illuminating said located cell with said illumination means and detecting a first activation response;
   (f) washing said cells to substantially remove all of said general mitogen;
   (g) further contacting said cells with said specific substance, locating said previously located cell, illuminating said cell with said illumination means and with said means for detecting measuring a second activation response; and
   (h) relating said first and said second activation responses to determine the state of sensitization of said cells to said particular substance.

13. The method of claim 12 wherein the generalized cytometry instrument further comprises translocating means for providing comparative motion between the illumination means, means for detecting and said surface means, said translocating means acting in cooperation with said means for controlling and said cell locating means whereby different immobilized cells may be illuminated and their respective responses detected.

14. The method as presented in claim 13 further comprising the step of contacting said cells at least once with a dye or a labeled probe whereby illumination from said illumination means interacts with said dye or labeled probe to provide a detectable activation response.

15. A method for measuring the presence and/or sensitizing effects of a specific substance in a sample fluid comprising the steps of:

(a) providing reagent cells capable of being sensitized by the substance to be detected and immobilizing said cells on surface means of a generalized cytometry instrument as provided in claim 1;
(b) contacting said cells with the fluid sample containing the specific substance to be detected;
(c) locating a cell with said cell locating means;
(d) illuminating said located cell with said illumination means and with means for detecting measuring a first activation response;
(e) washing said cells to substantially remove substantially all of said sample;
(f) further contacting said cells with a general mitogen;
(g) locating said previously located cell;
(h) illuminating said cell with said illuminating means and with said means for detecting measuring a second activation response; and
(i) relating said first activation and second activation responses to determine the presence and/or sensitizing effect of said specific substance in said sample fluid.

16. The method of claim 15 wherein the generalized cytometry instrument further comprises translocating means for providing comparative motion between the illumination means, means for detecting and said surface means, said translocating means acting in cooperation with said means for controlling and said cell locating means whereby different immobilized cells may be illuminated and their respective responses detected.

17. The method as presented in claim 16 further comprising the step of contacting said cells at least once with a dye or a labeled probe whereby illumination from said illumination means interacts with said dye or labeled probe to provide a detectable activation response.

18. A method for measuring the presence and/or sensitizing effects of a specific substance in a sample fluid comprising the steps of:
(a) providing reagent cells capable of being sensitized by the substance to be detected and immobilizing said cells on surface means of a generalized cytometry instrument as provided in claim 1;
(b) contacting said cells with a general mitogen;
(c) locating a cell with said cell locating means;
(d) illuminating said cell with said illumination means and with said means for detecting measuring a first activation response;
(e) further contacting said cells with a fluid sample containing the specific substance to be detected;
(f) locating said previously located cell,
(g) illuminating said cell with said illuminating means and with said means for detecting measuring a second activation response; and
(h) relating said first activation and second activation responses to determine the presence and/or sensitizing effect of said specific substance in said sample fluid.

19. The method of claim 18 wherein the generalized cytometry instrument further comprises translocating means for providing comparative motion between the illumination means, means for detecting and said surface means, said translocating means acting in cooperation with said means for controlling and said cell locating means whereby different immobilized cells may be illuminated and their respective responses detected.

20. The method as presented in claim 19 further comprising the step of contacting said cells at least once with a dye or a labeled probe whereby illumination from said illumination means interacts with said dye or labeled probe to provide a detectable activation response.

21. A method for measuring the activation of cells contained in a sample comprising the steps of:
(a) immobilizing the cells in said sample on surface means of a generalized cytometry instrument as provided in claim 1;
(b) contacting said cells with synthetic peptides corresponding to activation sites of proteins coded for by oncogenes or virus;
(c) locating a cell with said cell locating means; and
(d) illuminating said cells with said illumination means and with said means for detecting, measuring a response of said cells for determining the level of cell activation.

22. The method of claim 21 wherein the generalized cytometry instrument further comprises translocating means for providing comparative motion between the illumination means, means for detecting and said surface means, said translocating means acting in cooperation with said means for controlling and said cell locating means whereby different immobilized cells may be illuminated and their respective responses detected.

23. The method as presented in claim 22 further comprising the step of contacting said cells at least once with a dye or a labeled probe whereby illumination from said illumination means interacts with said dye or labeled probe to provide a detectable activation response.

24. The method of claim 23 wherein the surface means further comprises an immobilizing agent selected from the group consisting of agarose and antibodies specific for a determinant associated with said cells to be immobilized; said cell locating means comprises a helium-neon laser, said illumination means comprises an argon-ion laser, and said means for controlling a central processing unit.

25. The method of claim 21 wherein said step of measuring a response is performed a plurality of times.

26. A method of detecting one or more cellular properties as a function of time comprising:
(a) immobilizing said cells;
(b) locating at least two cells and recording their respective positions;
(c) reacting said cells with at least one reagent;
(d) measuring at least one property of each cell and recording said measurement with each respective cell;
(e) performing step (d) a plurality of times; and
(f) displaying said measured cellular property as a function of time.

27. The method as provided in claim 26 further comprising after step (d) the step of further reacting said cells with another reagent different from said first reagent and then performing steps (e) and (f).

28. A generalized cytometry instrument for repetitively measuring properties of live cells comprising:
(a) surface means for immobilizing the cells to be studied;
(b) illumination means for determining the location of at least two cells on said surface means in one mode of operation, said illumination means capable of operating in a second mode whereby suitable illumination of located cells may be provided to illicit a detectable response from said located cell;

(c) detector means for detecting said response from said located cell when said illumination means is operating in said second mode;

(d) means for controlling coupled to said illumination means for storing said cellular positions determined during said first operating mode and for operating said illumination means in said second mode; said means for controlling also coupled to said detector means for recording said cellular detectable response when said illumination means is operated in said second mode; and (e) means for display coupled to said means for controlling whereby said cellular response may be provided as a function of time.

29. The generalized cytometry instrument as provided in claim 1 wherein the time length of illumination provided in said second operating mode is adjusted in response to the number of located cells to be studied whereby sensitivity is improved.

30. The generalized cytometry instrument as provided in claim 1 wherein the illumination provided by said illumination means is adjusted in response to the number of located cells to be studied whereby sensitivity is improved.

31. The method of claim 26 wherein said step of measuring at least one property comprises measuring fluorescence for a period of time until a given integral of photons is obtained and determining the inverse of said period of time required whereby said inverse of illumination time may be displaced as a representation of the number of fluorescent sites per cell.

* * * * *